United States Patent
Shiono et al.

(10) Patent No.: US 8,698,079 B2
(45) Date of Patent: Apr. 15, 2014

(54) METHOD FOR SCANNING ELECTRON MICROSCOPE OBSERVATION OF SAMPLE FLOATING ON LIQUID SURFACE

(75) Inventors: Masamichi Shiono, Hitachinaka (JP); Masako Nishimura, Hitachinaka (JP); Mami Konomi, Hitachinaka (JP); Susumu Kuwabata, Ibaraki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/877,710

(22) PCT Filed: Sep. 16, 2011

(86) PCT No.: PCT/JP2011/005234
§ 371 (c)(1),
(2), (4) Date: May 17, 2013

(87) PCT Pub. No.: WO2012/046396
PCT Pub. Date: Apr. 12, 2012

(65) Prior Publication Data
US 2013/0221217 A1   Aug. 29, 2013

(30) Foreign Application Priority Data

Oct. 8, 2010  (JP) ................................ 2010-228064

(51) Int. Cl.
*H01J 37/20*   (2006.01)
(52) U.S. Cl.
USPC ............................ 250/307; 250/306; 250/310
(58) Field of Classification Search
USPC ......................... 250/306, 307, 310
See application file for complete search history.

(56) References Cited

U.S. PATENT DOCUMENTS

| | | | |
|---|---|---|---|
| 7,880,144 B2* | 2/2011 | Kuwabata et al. | 250/311 |
| 8,343,769 B2* | 1/2013 | Kinoshita et al. | 436/18 |
| 2005/0065020 A1* | 3/2005 | Holbrey et al. | 502/162 |
| 2009/0173882 A1* | 7/2009 | Kuwabata et al. | 250/307 |
| 2011/0057100 A1* | 3/2011 | Nakazawa et al. | 250/307 |
| 2013/0221217 A1* | 8/2013 | Shiono et al. | 250/307 |

FOREIGN PATENT DOCUMENTS

| | | |
|---|---|---|
| JP | 2007-203205 A | 8/2007 |
| JP | 2009-257848 A | 11/2009 |
| JP | 2009-266741 A | 11/2009 |
| JP | 2010-025656 A | 2/2010 |
| JP | 2010-133710 A | 6/2010 |
| WO | 2007/083756 A1 | 7/2007 |

* cited by examiner

*Primary Examiner* — David A Vanore
(74) *Attorney, Agent, or Firm* — Mattingly & Malur, PC

(57) ABSTRACT

A micro sample floating on the surface of an ionic liquid is observed by scanning electron microscopy without the sample being covered with the ionic liquid. A floating or hydrophobic sample is floated on the surface of a hydrophilic ionic liquid aqueous solution to prevent the micro sample from being covered with the ionic liquid. A hydrophobic ionic liquid is used for hydrophilic samples. With the use of an ionic liquid aqueous solution of low viscosity and large flowability, the micro sample is allowed to freely aggregate, disperse, and align on the surface of the ionic liquid, and to refloat even when settled in the ionic liquid. For easy observation with a scanning electron microscope, the ionic liquid aqueous solution is dried to lower the flowability of the ionic liquid aqueous solution, after the form of the micro sample has stabilized and before electron microscope observation.

6 Claims, 7 Drawing Sheets

METHOD FOR SCANNING ELECTRON MICROSCOPE OBSERVATION OF SAMPLE FLOATING ON LIQUID SURFACE

TECHNICAL FIELD

An embodiment of the present invention relates to a method for electron microscope observation of micro samples floating on an ionic liquid, specifically for electron microscope observation of sample aggregation and dispersion, orientation of individual samples, and the like.

BACKGROUND ART

A micro sample floating on a liquid surface aggregates, disperses, and aligns in different ways as determined by hydrophilicity and hydrophobicity. There is also a phenomenon in which individual particles align in specific directions as determined by physical conditions such as magnetic field, electric field, pressure, and temperature. Further, a technique is available that takes advantage that a micro sample on a liquid surface is not fixed, and freely controls the direction of the micro sample by controlling physical conditions such as magnetic field, electric field, pressure, and temperature. Observing such floating forms under an electron microscope is important in analyzing the physical properties of functional substances such as catalysts, drugs, and cosmetics, and fine crystals and organic powder materials, and the biology of small biological materials. It is, however, difficult with conventional techniques to make a high-magnification observation of a micro sample floating on a liquid surface. This is because the aqueous solution and the organic solvent evaporate in the vacuum environment of electron microscope observation.

As a countermeasure, a technique is proposed that makes an electron microscope observation after freezing a liquid below a freezing point, using a cool stage or a cryo stage. However, the technique is problematic, because the freezing of a liquid changes the shape of the micro sample, or the form of the micro sample, causing the micro sample to aggregate, disperse, align, or orientate differently. Another problem is that, despite the frozen sample, the water component evaporates in a vacuum. It, then, might be possible to use a technique that makes use of an oil as a liquid material that does not evaporate in a vacuum environment. However, a problem of such a technique is that the sample floating on the oil surface rapidly undergoes flowing movement under electron beam irradiation. The technique also has the charging problem. In another proposed method, a liquid is placed under atmospheric pressure, and a thin film is used to separate the liquid from the vacuum environment inside the tube of an electron microscope. However, the method still fails to enable observation of a micro sample floating on a liquid surface.

There is also a method in which a micro sample is sprinkled over a carbon paste or the like to mimic the floating of a micro sample on a liquid. This technique solves the charging problem, and does not involve flowability. The method thus advantageously makes the electron microscope observation easier. However, because the carbon paste quickly solidifies, the micro sample is quickly fixed before it fully aggregates, disperses, aligns, or orients. Thus, it cannot be said that the method successfully reproduces the form of a micro sample floating on a liquid surface. Further, because the micro sample is quickly fixed once being sprinkled over the carbon paste, it is not possible to control the direction of individual particles.

As a countermeasure, a technique is developed that uses an ionic liquid for the observation and control of a micro sample in a liquid under an electron microscope. For example, PTL 1 (WO2007/083756) solves the charging problem by applying an ionic liquid to a sample surface, and enables the actual shape of a sample to be observed with a scanning electron microscope and a transmission electron microscope.

PTL 2 (JP-A-2009-266741) enables observation of a sample floating on an ionic liquid after the sample is introduced into the ionic liquid held in a microgrid, a mesh, or the like.

PTL 3 (JP-A-2010-25656) applies an ionic liquid to a sample to prevent a sample surface from being exposed to the atmosphere.

CITATION LIST

Patent Literature

PTL 1: WO2007/083756
PTL 2: JP-A-2009-266741
PTL 3: JP-A-2010-25656

SUMMARY OF INVENTION

Technical Problem

The techniques of the related art have the following problems. In the invention described in PTL 1, because an ionic liquid is applied to a sample surface, the original fine structure of the sample, or the micro sample itself is buried in the ionic liquid. The invention described in PTL 2 enables a sample in an ionic liquid to be observed through a transmission electron microscope. However, the technique does not allow for observation through a scanning electron microscope unless the sample is exposed to the ionic liquid surface, and requires moving a sample holder to control the sample direction. PTL 3 applies an ionic liquid to a sample surface, and the original fine structure of the sample, or the micro sample itself is buried in the ionic liquid.

It is accordingly an object of an embodiment of the present invention to realize a technique whereby a micro sample floating on an ionic liquid surface can be observed with a scanning electron microscope without being covered with the ionic liquid, and in which the form of the micro sample aggregating, dispersing, and aligning on a liquid surface can be naturally maintained as it occurs, and the orientation or direction of individual micro samples can be controlled.

Solution to Problem

A floating or hydrophobic sample is floated on a surface of a hydrophilic ionic liquid aqueous solution to prevent the micro sample from being covered with the ionic liquid. A hydrophobic ionic liquid is used for hydrophilic samples. With the use of an ionic liquid aqueous solution of low viscosity and large flowability, the micro sample is allowed to freely aggregate, disperse, and align on the surface of the ionic liquid, and to refloat even when settled in the ionic liquid. For easy observation with a scanning electron microscope, the ionic liquid aqueous solution is dried to lower the flowability of the ionic liquid aqueous solution, after the form of the micro sample has stabilized and before electron microscope observation.

The conventional problems are solved by observing the micro sample under a scanning electron microscope after these pretreatments. Further, the direction and orientation of individual micro samples are controlled with the hydrophobic ionic liquid and the hydrophilic ionic liquid used for different purposes.

Advantageous Effects

The technique of the embodiment of the present invention whereby a floating or hydrophobic sample is observed as it floats on the surface of a hydrophilic ionic liquid aqueous solution is advantageous, because the technique enables electron microscope observation of the aggregation, dispersion, or alignment state of the micro sample on the liquid surface as it naturally occurs. Because a hydrophilic ionic liquid and a hydrophobic ionic liquid are used for hydrophobic samples and hydrophilic samples, respectively, the ionic liquid is prevented from adhering to the sample surface, and the micro sample or the fine structure of a sample surface can be observed. Further, because the unnecessary components are precipitated in the ionic liquid, the floating or hydrophobic sample can easily be observed under an electron microscope.

In the case of a partially hydrophilic sample, only the hydrophilic surface contacts the ionic liquid, making it possible to direct the hydrophobic portion in the direction of the detector of an electron microscope. Because the sample is directed in the opposite direction in a hydrophobic ionic liquid, and the hydrophilic portion also can be directed in the direction of the detector of the electron microscope. The embodiment of the present invention thus advantageously enables the sample orientation to be controlled with the hydrophilic or hydrophobic ionic liquid used for different purposes.

The embodiment of the present invention is particularly effective for the scanning electron microscope observation of small biological materials (such as cultured cells, floating planktons, and pollens), functional substances (such as catalysts, drugs, and cosmetics), hydrophobic or hydrophilic resins, and amphipathic substances.

DESCRIPTION OF EMBODIMENTS

Examples of the present invention are described below with reference to the accompanying drawings.

Example 1

Figure 1:
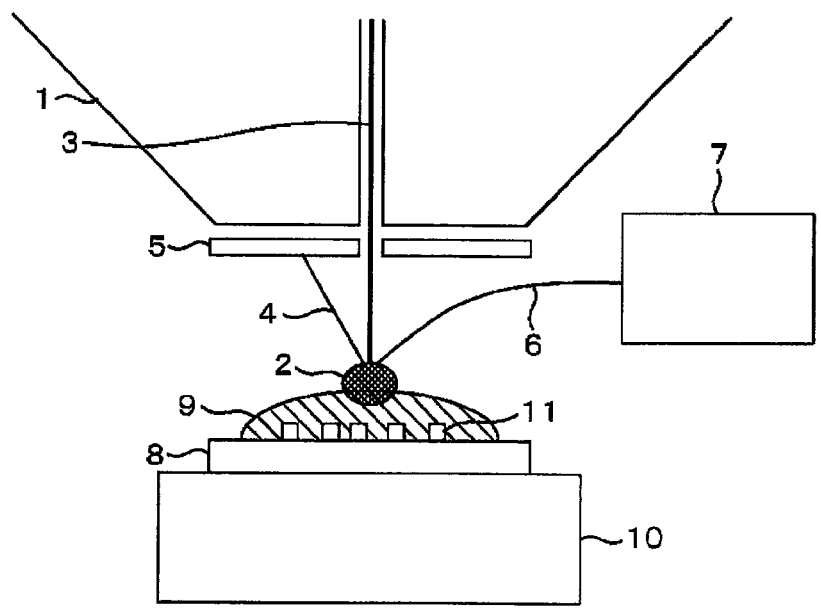
FIG. 1 is a side view of a sample chamber of an electron microscope of Example 1.
Figure 2:
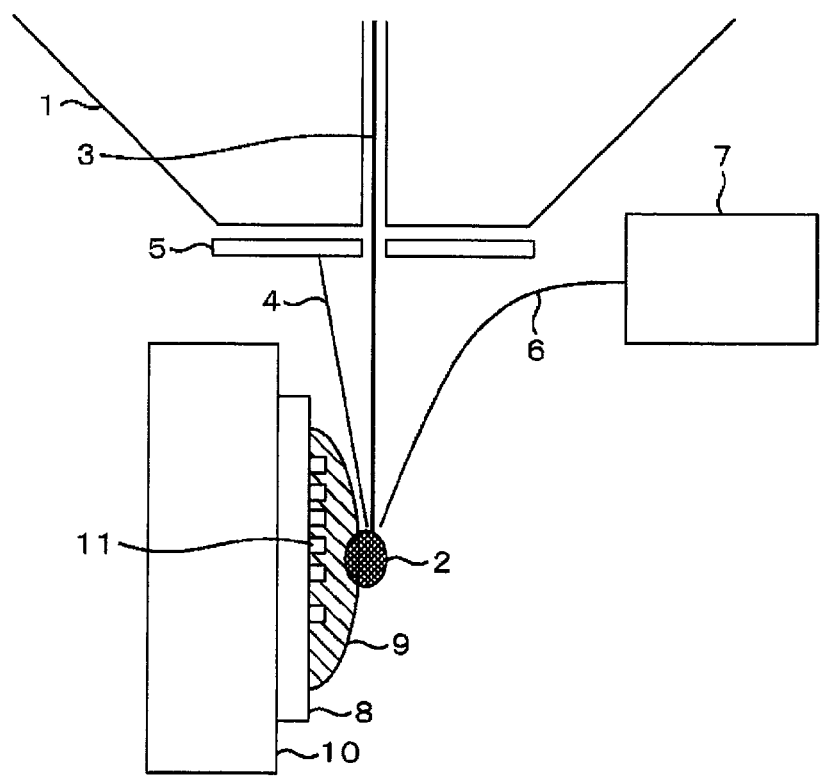
FIG. 2 is an explanatory diagram illustrating a sample tilted 90° relative to the side view of the sample chamber of the electron microscope of Example 1.

FIG. 1 is a side view of a sample chamber of an electron microscope of the present example. The electron microscope of the present example is a scanning electron microscope, and inside the sample chamber are an electron microscope objective lens 1, an electron beam 3 that irradiates a sample 2 through the electron microscope objective lens 1, a reflected electron detector 5 that detects a reflected electronic signal 4 from the sample 2, and a secondary electron detector 7 that detects a secondary electronic signal 6 from the sample 2. The sample 2 floats on the surface of an ionic liquid 9 dropped onto a silicon wafer 8. In the present example, the ionic liquid 9 is dropped on the silicon wafer 8 fixed on an electron microscope sample stage 10. However, the ionic liquid 9 may be directly dropped on the electron microscope sample stage 10. Impurities 11 contained in the sample are settled at the bottom of the droplets of the ionic liquid 9. However, because the ionic liquid 9 appears opaque under the electron microscope, the impurities 11 are unobservable by electron microscopy. In the present example, the sample 2 can be fixed onto the surface of the ionic liquid 9, and can thus be observed also from the side surface upon tilting the electron microscope sample stage 10 at right angle as shown in FIG. 2.

The present example describes a technique whereby a small biological material on the ionic liquid is observed, using as a sample the phytoplankton *Chromophyton rosanoffii* having a liquid floating property. The example described herein is not limited to *Chromophyton rosanoffii*, and is also applicable to observation of other small biological materials such as arthropods, planktons, and cultured cells, and other materials having lighter densities than the ionic liquid or ionic liquid solution, including floating samples, functional substances such as drugs and cosmetics, fine crystals, and organic powder materials.

Figure 3:
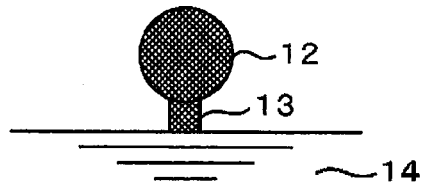
FIG. 3 is a schematic diagram of *Chromophyton rosanoffii* of Example 1.
Figure 4:
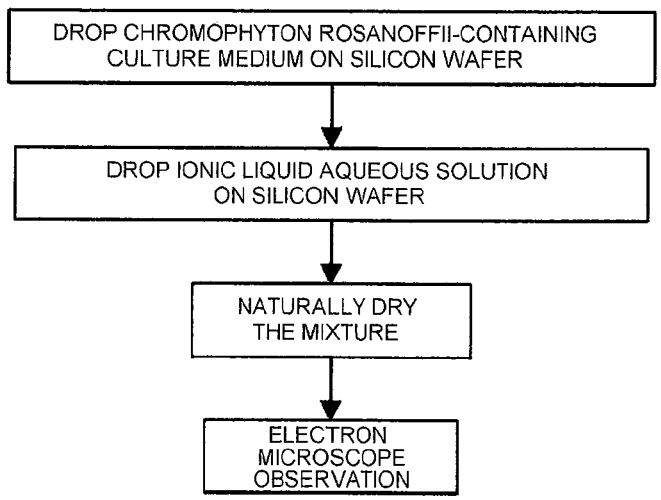
FIG. 4 is an explanatory diagram representing the procedure of obtaining an electron micrograph of *Chromophyton rosanoffii* with the technique of Example 1.
Figure 5:
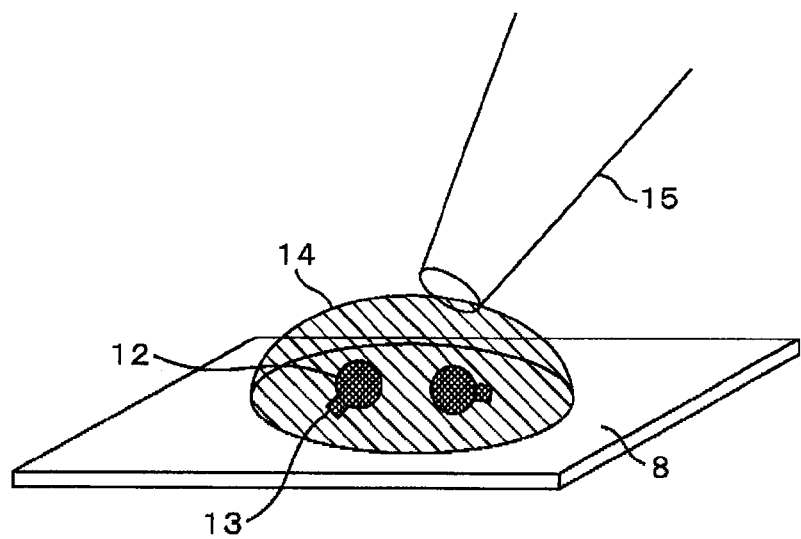
FIG. 5 is an explanatory diagram illustrating how a culture medium containing *Chromophyton rosanoffii* is dropped onto a silicon wafer in Example 1.

FIG. 3 is a schematic diagram of *Chromophyton rosanoffii*. As illustrated in FIG. 3, the *Chromophyton rosanoffii* is composed of a cell body 12 and a stalk portion 13, and floats on a culture medium 14 with the stalk portion in contact with the liquid surface. FIG. 4 is an explanatory diagram representing the procedure of obtaining an electron micrograph of the *Chromophyton rosanoffii* according to the embodiment of the present invention. Firstly, the culture medium containing *Chromophyton rosanoffii* is dropped on the silicon wafer. This state is represented by the explanatory diagram shown in FIG. 5. A metallic sample stage for electron microscopy may be used instead of the silicon wafer. In this case, the sample stage should preferably have a flat surface. Referring to FIG. 5, the culture medium 14 containing *Chromophyton rosanoffii* uses the habitat pond water of *Chromophyton rosanoffii*, and is an aqueous solution containing salts. Referring to FIG. 5, a graduated micropipette is desirable as the device 15 used to drop the *Chromophyton rosanoffii*-containing culture medium. However, an ungraduated pipette also may be used when the dropped amount of the culture medium does not need to be specified. The optimum drop amount of the culture medium depends on the silicon wafer or the sample stage. The appropriate amount is about 20 µl for about 1 cm$^2$ sizes.

Figure 6:
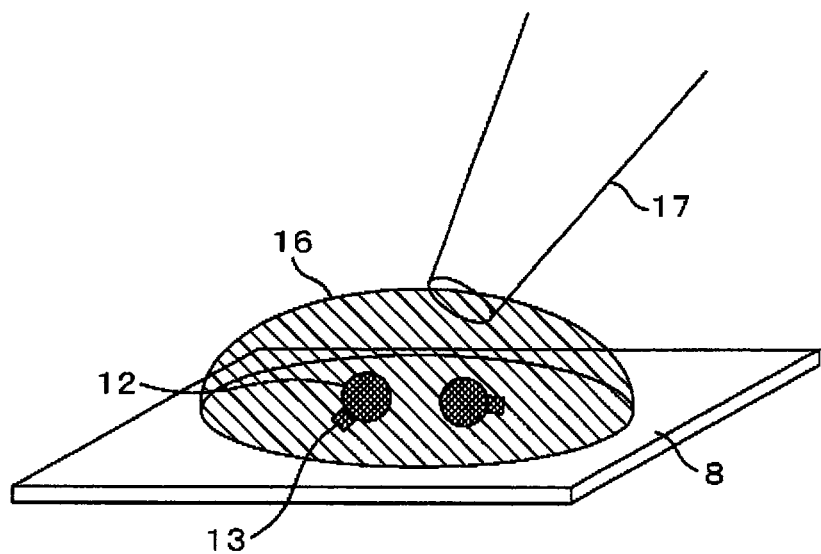
FIG. 6 is an explanatory diagram illustrating how a culture medium containing *Chromophyton rosanoffii* is added to an ionic liquid aqueous solution to prepare a mixture 16 of the culture medium and the ionic liquid in Example 1.

As represented in the explanatory diagram of FIG. 6, the ionic liquid aqueous solution is added to the *Chromophyton rosanoffii*-containing culture medium to prepare a mixture 16 of the culture medium and the ionic liquid. The ionic liquid aqueous solution is prepared by diluting the ionic liquid with distilled water, and has a concentration of desirably 20% or less. Higher ionic liquid concentrations make the drying insufficient, and fluidize the ionic liquid. This may cause trouble in electron microscope observation. The present example uses *Chromophyton rosanoffii* having a hydrophobic property, and thus uses a hydrophilic ionic liquid ($C_8H_{15}N_2BF_4$). It is desirable to use a hydrophobic ionic liquid for hydrophilic samples. Referring to FIG. 6, a graduated micropipette is desirably used as the device 17 used to drop the ionic liquid aqueous solution. However, an ungraduated pipette also may be used when the dropped amount of the ionic liquid does not need to be specified. The optimum drop amount of the ionic liquid aqueous solution depends on the amount of the culture medium, and it is desirable to drop the ionic liquid aqueous solution in smaller amounts than the amount of the culture medium. In the present example, the ionic liquid aqueous solution is dropped onto the *Chromophyton rosanoffii*-containing culture medium. Conversely, the *Chromophyton rosanoffii*-containing culture medium may be dropped onto the ionic liquid.

Figure 7:
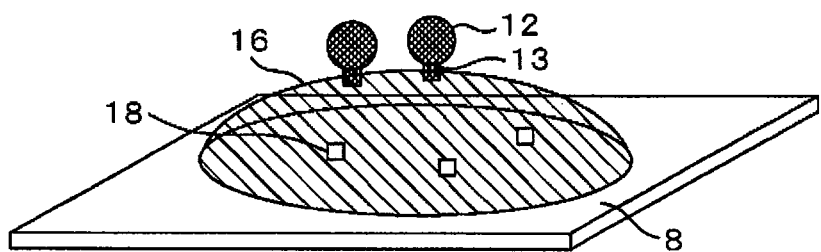
FIG. 7 is an explanatory diagram illustrating a state after at least 3 hours from addition of the ionic liquid aqueous solution to the *Chromophyton rosanoffii*-containing culture medium in Example 1.

FIG. 7 depicts a state after at least 3 hours from the addition of the ionic liquid aqueous solution to the culture medium. By being left unattended for at least 3 hours, the cell body 11 of the *Chromophyton rosanoffii* surfaces with the stalk portion 12 in contact with the mixture 16 of the culture medium and the ionic liquid, as illustrated in FIG. 7. Here, note that the surface time of the *Chromophyton rosanoffii* varies according to the growth conditions of the *Chromophyton rosanoffii*, and the 3-hour unattended time period should be taken as an indication. The water component in the mixture 16 of the culture medium and the ionic liquid evaporates over the long unattended time, and the volume shrinks to make the shape of the droplets thinner, like a thin film. The water component in the mixture 16 of the culture medium and the ionic liquid mostly originates in the culture medium. Because the culture medium contains salt components, the salt components in the culture medium crystallize with increase in the salt concentration following the drying. Referring to FIG. 7, the crystallized salt components 18 reside in the mixture 16 of the culture medium and the ionic liquid, and can be observed through a light microscope or by visual inspection.

Electron microscopy is possible in the state of FIG. 7, provided that the mixture of the culture medium and the ionic liquid is sufficiently dried. When the drying appears to be insufficient, the mixture may be dried in a vacuum environment. A vacuum degassing device with an observation window can effectively be used for pretreatment or safety measures before introducing the sample in the sample chamber of the electron microscope, because such a device can check for the presence or absence of bumping. However, when the drying time after adding the ionic liquid aqueous solution to the culture medium is about 3 hours, the *Chromophyton rosanoffii* may rapidly undergo flowing movement under the electron microscope because of the remaining flowability of the mixture of the culture medium and the ionic liquid. It is therefore preferable to use as long a drying time as possible. It is, however, possible to reduce the drying time with the use of a drying device.

Figure 8:
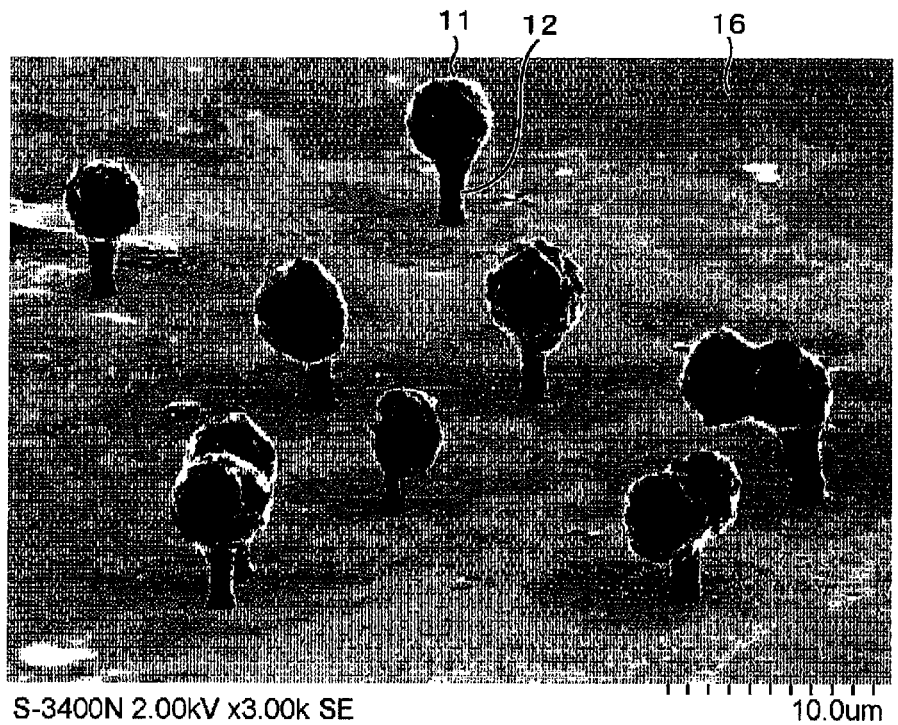
FIG. 8 is an explanatory diagram representing an electron micrograph of the *Chromophyton rosanoffii* actually observed under an electron microscope by using the method of Example 1, demonstrating that observation of *Chromophyton rosanoffii* is indeed possible with the method of Example 1.

FIG. 8 represents an example in which the method of the present example was actually used to observe *Chromophyton rosanoffii* with the electron microscope. FIG. 8 shows the cell body 11 and the stalk portion 12 of the *Chromophyton rosanoffii*, and the mixture 16 of the culture medium and the ionic liquid. In this observation example, the sample is tilted 70°. However, because the flow of the mixture of the culture medium and the ionic liquid is minimized, the *Chromophyton rosanoffii* remains upright.

Figure 9:
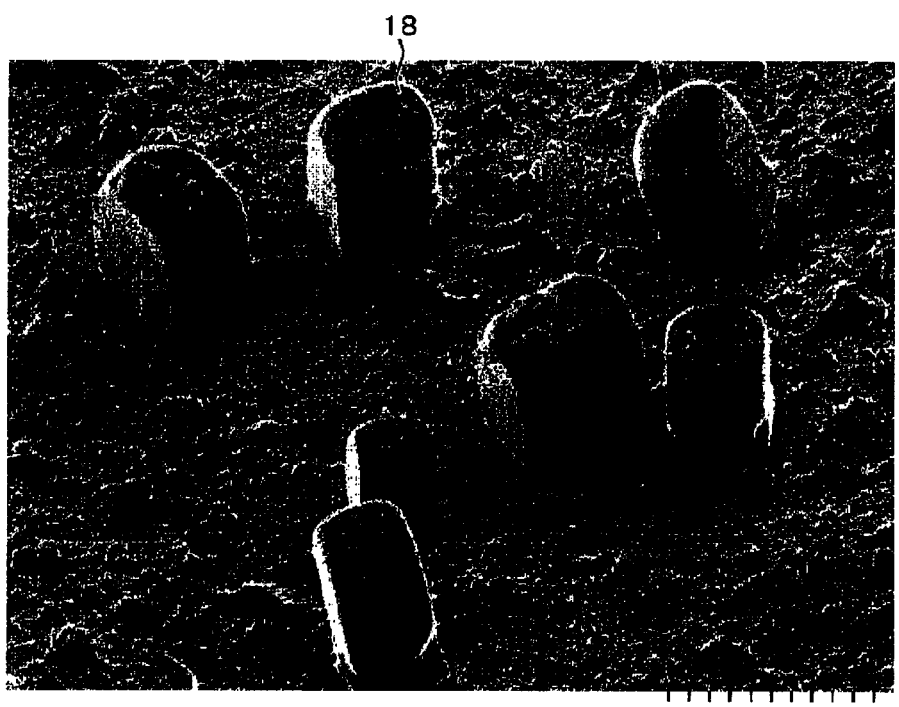
FIG. 9 is an explanatory diagram representing an electron micrograph of the *Chromophyton rosanoffii* in a culture medium observed under an electron microscope without using an ionic liquid, demonstrating that only the observation of crystals of salts originating in the culture medium is possible, and that the *Chromophyton rosanoffii* is unobservable.

As a reference, FIG. 9 represents an example in which *Chromophyton rosanoffii* was observed without using the method of the present example. Without the ionic liquid, the salts originating in the *Chromophyton rosanoffii* culture medium crystallize, and become an obstacle of *Chromophyton rosanoffii* observation. Further, because the culture medium completely dries, the *Chromophyton rosanoffii* floating on the liquid cannot be observed. The salt crystals are indicated by reference numeral 18 in FIG. 9.

Referring to FIG. 8, with the method of the present example, the salt crystals are believed to either precipitate or dissolve in the mixture of the culture medium and the ionic liquid. Because the mixture of the culture medium and the ionic liquid appears opaque under the electron microscope, the salts precipitated in the mixture are not observed. This makes it easier to observe the *Chromophyton rosanoffii*.

Example 2

The present example describes a method for easy observation of pollens by electron microscopy, whereby only pollens are separated onto the ionic liquid from pollens containing sand grains. The technique is not limited to pollens, and is also applicable to observation of small biological materials such as spores, mites, and insects, and floating samples or hydrophobic samples having lighter densities than water.

Figure 10:
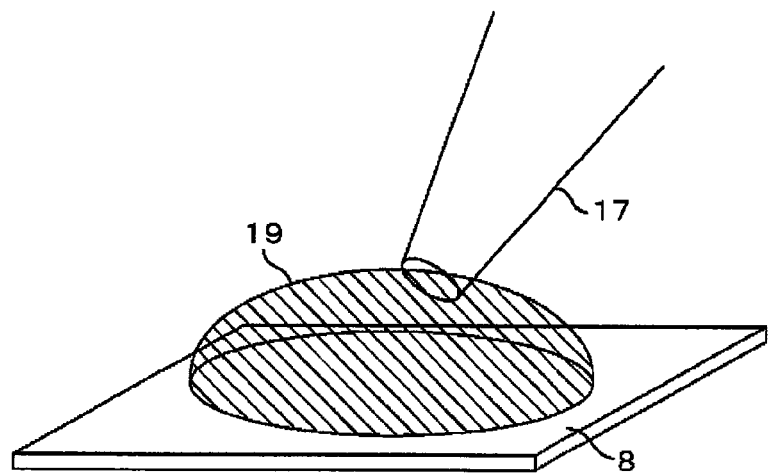
FIG. 10 is an explanatory diagram illustrating how an ionic liquid aqueous solution is dropped onto a silicon wafer in Example 2.

First, an ionic liquid aqueous solution is dropped onto a silicon wafer. This state is represented by the explanatory diagram shown in FIG. 10. A metallic sample stage for electron microscopy may be used instead of the silicon wafer. In this case, the sample stage should preferably have a smooth surface. Referring to FIG. 10, a graduated micropipette is desirable as the device 17 used to drop the ionic liquid aqueous solution. However, an ungraduated pipette also may be used when the dropped amount of the ionic liquid aqueous solution does not need to be specified. The optimum drop amount of the ionic liquid aqueous solution depends on the silicon wafer or the sample stage. The appropriate amount is about 20 µl for about 1 cm$^2$ sizes. Referring to FIG. 10, an ionic liquid aqueous solution 19 is prepared by diluting the ionic liquid with distilled water, and has a concentration of desirably 5% or less, or as low as 1%. Higher ionic liquid concentrations make the drying insufficient, and fluidize the ionic liquid. This may cause trouble in electron microscope observation. The viscosity of the ionic liquid aqueous solution lowers as the concentrations of the ionic liquid becomes smaller. Thus, lower concentrations make it easier to spread the ionic liquid aqueous solution over the silicon wafer. Removing the water component from the ionic liquid aqueous solution in the subsequent drying makes the ionic liquid aqueous solution 19 even thinner, like a thin film.

The present example uses the hydrophilic ionic liquid ($C_8H_{15}N_2BF_4$). However, it is desirable to use a hydrophobic ionic liquid for samples with a hydrophilic property.

Figure 11:
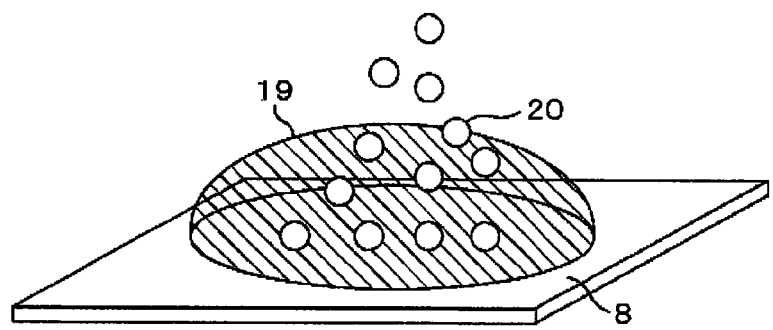
FIG. 11 is an explanatory diagram illustrating how pollens are sprinkled over an ionic liquid aqueous solution in Example 2.

Thereafter, as illustrated in FIG. 11, the pollens 20 are sprinkled over the ionic liquid aqueous solution 19, and left unattended for a whole day to dry the unnecessary water component. Here, the pollens 20 may be sprinkled after the ionic liquid aqueous solution is left unattended for a whole day to sufficiently dry. Desirably, the ionic liquid aqueous solution is left unattended for a whole day to remove the unnecessary water component. However, the unattended time may be reduced by reducing the drop amount of the ionic liquid aqueous solution, or with the use of a drying device. When sprinkled before drying the ionic liquid aqueous solution, the pollens are partially buried into the ionic liquid aqueous solution on the liquid surface after the solution is dried. However, the pollens are desirably fixed even in this case. On the other hand, when sprinkled after drying the ionic liquid aqueous solution, the pollens do not bury into the ionic liquid, and are desirably observable. In either case, impurities, for example, such as sand grains having larger specific gravities than the ionic liquid aqueous solution settle in the ionic liquid, and are separated from the target pollens. The ionic liquid appears opaque under the scanning electron microscope, and impurities such as sand grains are unobservable in the field of the scanning electron microscope.

The pollens can be observed by electron microscopy regardless of whether being sprinkled before or after drying the ionic liquid aqueous solution, provided that the water component in the ionic liquid aqueous solution is sufficiently evaporated. For sufficient drying, vacuum drying may be performed before electron microscope observation.

Figure 12:
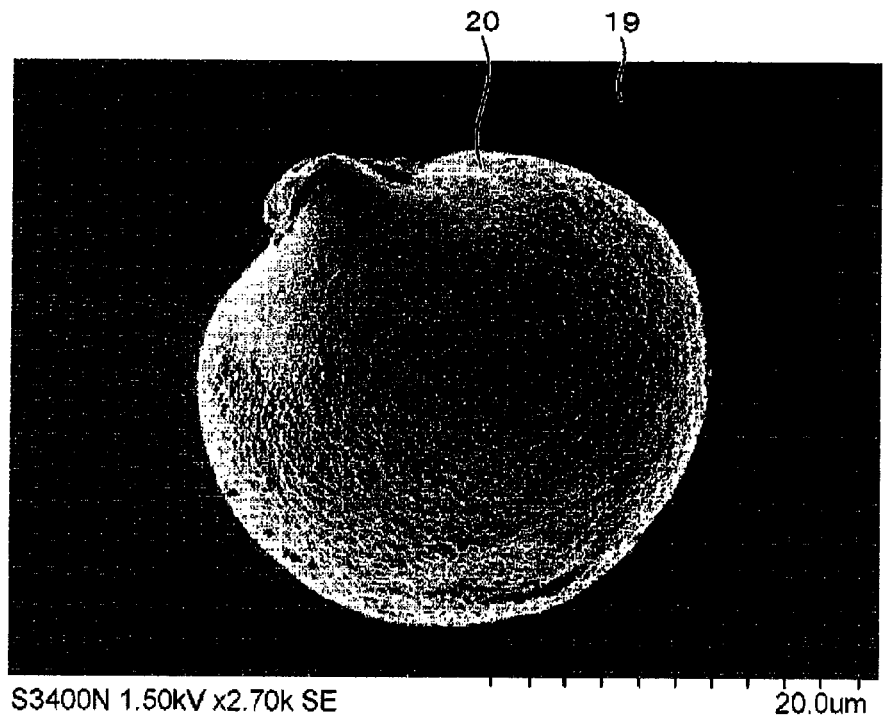
FIG. 12 is an explanatory diagram representing an electron micrograph of the pollens actually observed under an electron microscope by using the method of Example 2, demonstrating that observation of pollens is indeed possible with the method of Example 2.

FIG. 12 represents an electron micrograph of a pollen sprinkled after drying the ionic liquid aqueous solution. FIG. 12 shows the ionic liquid aqueous solution 19, and the pollen 20. The pollen 20 is fixed without being buried into the ionic liquid aqueous solution 19.

Example 3

Figure 13:
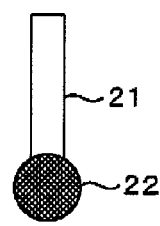
FIG. 13 is an explanatory diagram schematically illustrating a partially hydrophilic hydrophobic-sample of Example 3.

The present example describes a method whereby a partially hydrophilic hydrophobic-sample is fixed in a certain sample orientation. FIG. 13 schematically represents the partially hydrophilic hydrophobic-sample. As illustrated in FIG. 13, the partially hydrophilic hydrophobic-sample is a sample composed of a hydrophobic portion 21 and a hydrophilic portion 22.

Figure 14:
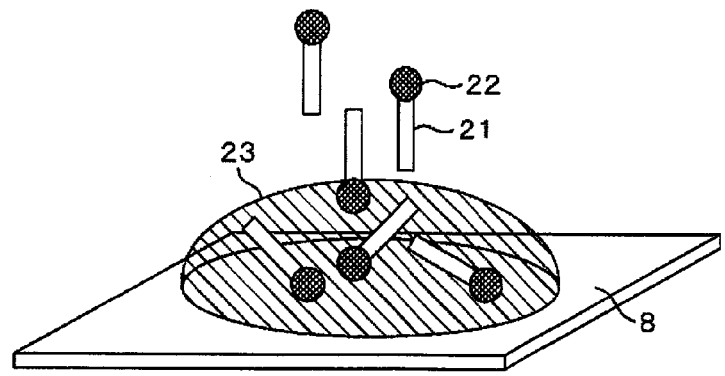
FIG. 14 is an explanatory diagram representing the procedure of sprinkling a partially hydrophilic hydrophobic-sample after dropping a hydrophilic ionic liquid aqueous solution onto a silicon wafer in Example 3.

First, a hydrophilic ionic liquid aqueous solution 23 is dropped onto a silicon wafer, as illustrated in FIG. 14. A metallic sample stage for electron microscopy may be used instead of the silicon wafer. In this case, the sample stage should preferably have a flat surface. The optimum drop amount of the ionic liquid aqueous solution depends on the silicon wafer or the sample stage. The appropriate amount is about 20 µl for about 1 cm$^2$ sizes. The ionic liquid aqueous solution is prepared by diluting the ionic liquid with distilled water, and has a concentration of desirably 5% or less, or as low as 1%. Thereafter, as illustrated in FIG. 14, a partially hydrophilic hydrophobic-sample is sprinkled over the hydrophilic ionic liquid aqueous solution 23, and left unattended for a whole day. When the partially hydrophilic hydrophobic-sample is contained in a solution, the sample-containing solution is dropped onto the ionic liquid aqueous solution with a pipette or the like. Conversely, the ionic liquid aqueous solution may be dropped onto the sample-containing solution.

Figure 15:
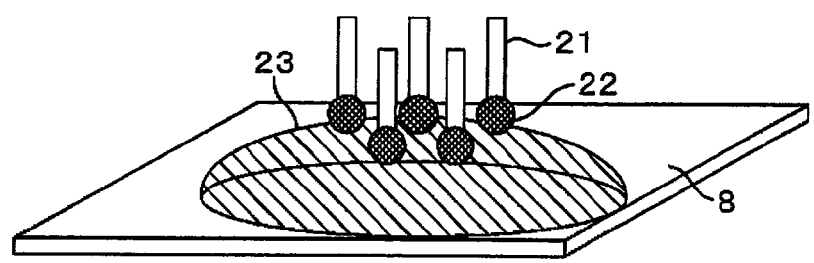
FIG. 15 is an explanatory diagram representing a state after the partially hydrophilic hydrophobic-sample sprinkled over an ionic liquid aqueous solution is left unattended for a certain time period in Example 3, showing that the direction is set with the hydrophobic portion directed upward.

The partially hydrophilic hydrophobic-sample is sprinkled over the ionic liquid aqueous solution, and left unattended for a certain time period. As a result, as illustrated in FIG. 15, the hydrophilic portion of the partially hydrophilic hydrophobic-sample comes into contact with the ionic liquid aqueous solution, and the direction is set with the hydrophobic portion 21 directed upward. The sample is firmly fixed on the surface of the ionic liquid aqueous solution upon evaporating the unnecessary water component. The sample treated in this fashion is ready for electron microscope observation in the state represented in FIG. 15.

Desirably, the ionic liquid aqueous solution is left unattended for a whole day to remove the unnecessary water component in the ionic liquid aqueous solution. However, the unattended time may be reduced by reducing the drop amount of the ionic liquid aqueous solution, or with the use of a drying device. This method is effective for the electron microscope observation of only the hydrophobic portion of the partially hydrophilic hydrophobic-sample.

Figure 16:
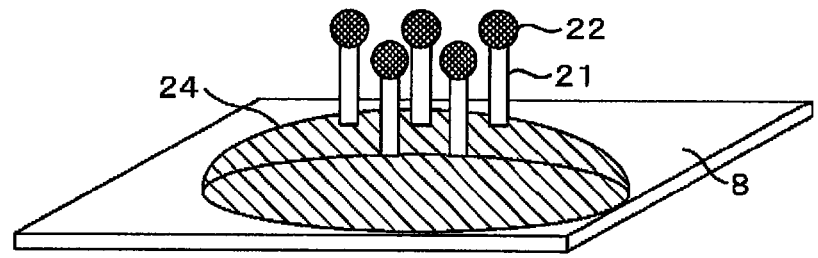
FIG. 16 is an explanatory diagram representing a state after the partially hydrophilic hydrophobic-sample sprinkled over a hydrophobic ionic liquid is left unattended for a certain time period in Example 3, showing that the direction is set with the hydrophilic portion directed upward.

On the other hand, for the observation of the hydrophilic portion of the partially hydrophilic hydrophobic-sample, the hydrophilic portion 22 may be directed upward with the use of a hydrophobic ionic liquid 24, as illustrated in FIG. 16.

REFERENCE SIGN LIST

1 Electron microscope objective lens
2 Sample
3 Electron beam
4 Reflected electronic signal
5 Reflected electron detector
6 Secondary electronic signal
7 Secondary electron detector
8 Silicon wafer
9 Ionic liquid
10 Electron microscope sample stage
11 Impurities
12 Cell body of *Chromophyton rosanoffii*
13 Stalk portion of *Chromophyton rosanoffii*
14 *Chromophyton rosanoffii*-containing culture medium
15 Device for dropping *Chromophyton rosanoffii*-containing culture medium
16 Mixture of *Chromophyton rosanoffii*-containing culture medium and ionic liquid
17 Device for dropping ionic liquid aqueous solution
18 Salt crystals
19 Ionic liquid aqueous solution
20 Pollen 21 Hydrophobic portion of partially hydrophilic hydrophobic-sample
22 Hydrophilic portion of partially hydrophilic hydrophobic-sample
23 Hydrophilic ionic liquid aqueous solution
24 Hydrophobic ionic liquid

The invention claimed is:

1. A specimen observation method for observing behaviors of a specimen on a surface of an ionic liquid, the method comprising floating a sample for scanning electron microscopy so as to allow a specimen to freely move, the ionic liquid including a cation and an anion, and being involatile or hardly volatile in a vacuum.

2. A method for preparing a specimen observed by scanning electron microscopy, the method comprising drying a low-viscosity ionic liquid aqueous solution after allowing a specimen to freely move inside or on a surface of the ionic liquid, and removing the water component to increase the viscosity of the ionic liquid aqueous solution and fix the specimen.

3. A method for preparing a specimen to be floated on an ionic liquid and used for scanning electron microscopy, the method comprising applying a low-viscosity ionic liquid solution onto a sample stage of an electron microscope, and sprinkling a powder specimen over the ionic liquid to fix the specimen.

4. A method for preparing a specimen to be floated on an ionic liquid and used for scanning electron microscopy according to claim 3, further comprising floating the specimen that includes a hydrophilic site and a hydrophobic site on a hydrophobic ionic liquid to direct the hydrophilic site in a direction of a detector of a scanning electron microscope.

5. A method for preparing a specimen to be floated on an ionic liquid and used for scanning electron microscopy according to claim 3, further comprising floating the specimen that includes a hydrophilic site and a hydrophobic site on a hydrophilic ionic liquid to direct the hydrophobic site in a direction of a detector of a scanning electron microscope.

6. A method for preparing a specimen to be floated on an ionic liquid and used for scanning electron microscopy according to claim 3, further comprising using an ionic liquid or an ionic liquid solution, and separating a specimen having a smaller specific gravity than the ionic liquid or the ionic liquid solution from an impurity having a larger specific gravity than the ionic liquid or the ionic liquid solution.

* * * * *